US00PP28653P3

(12) United States Plant Patent
Lodge

(10) Patent No.: US PP28,653 P3
(45) Date of Patent: Nov. 14, 2017

(54) ***POLEMONIUM* PLANT NAMED 'POLELODGE'**

(50) Latin Name: *Polemonium reptans*
Varietal Denomination: Polelodge

(71) Applicant: David Lodge, Wickford (GB)

(72) Inventor: David Lodge, Wickford (GB)

( * ) Notice: Subject to any disclaimer, the term of this patent is extended or adjusted under 35 U.S.C. 154(b) by 18 days.

(21) Appl. No.: 14/999,224

(22) Filed: Apr. 11, 2016

(65) Prior Publication Data

US 2017/0295709 P1 Oct. 12, 2017

(51) Int. Cl.
*A01H 5/02* (2006.01)

(52) U.S. Cl.
USPC ..... Plt./470

(58) Field of Classification Search
USPC ..... Plt./470
See application file for complete search history.

*Primary Examiner* — Susan McCormick Ewoldt
(74) *Attorney, Agent, or Firm* — C. A. Whealy

(57) ABSTRACT

A new and distinct cultivar of *Polemonium* plant named 'Polelodge', characterized by its basal clumping habit; dense and bushy appearance; numerous green and yellow variegated leaves; small violet blue-colored flowers; long flowering period; and good garden performance.

2 Drawing Sheets

Botanical designation: *Polemonium reptans.*
Cultivar denomination: 'POLELODGE'.

BACKGROUND OF THE INVENTION

The present invention relates to a new and distinct cultivar of *Polemonium* plant, botanically known as *Polemonium reptans*, commonly known as Jacob's Ladder and hereinafter referred to by the name 'Polelodge'.

The new *Polemonium* plant is a product of a planned breeding program conducted by the Inventor in Battlesbridge, Wickford, Essex, United Kingdom. The new *Polemonium* plant originated from an open-pollination in Battlesbridge, Wickford, Essex, United Kingdom of an unnamed selection of *Polemonium reptans*, not patented, as the female, or seed, parent, with an unknown selection of *Polemonium reptans* as the male, or pollen, parent. The new *Polemonium* plant was discovered and selected by the Inventor as a single flowering plant from within the progeny of the stated open-pollination in a controlled nursery environment in Battlesbridge, Wickford, Essex, United Kingdom in May, 2005.

Asexual reproduction of the new *Polemonium* plant by basal cuttings in a controlled greenhouse environment in Battlesbridge, Wickford, Essex, United Kingdom since June, 2005 has shown that the unique features of this new *Polemonium* plant are stable and reproduced true to type in successive generations.

SUMMARY OF THE INVENTION

Plants of the new *Polemonium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Polelodge'. These characteristics in combination distinguish 'Polelodge' as a new and distinct *Polemonium* plant:

1. Basal clumping habit.
2. Dense and bushy appearance.
3. Numerous green and yellow variegated leaves.
4. Small violet blue-colored flowers.
5. Long flowering period.
6. Good garden performance.

Plants of the new *Polemonium* and the female parent selection differ primarily in leaf color as plants of the female parent selection have solid green-colored leaves.

Plants of the new *Polemonium* can be compared to plants of *Polemonium reptans* 'Stairway to Heaven', disclosed in U.S. Plant Pat. No. 15,187. In side-by-side comparisons, plants of the new *Polemonium* and 'Stairway to Heaven' differ primarily in the following characteristics:

1. Plants of the new *Polemonium* are taller and broader than plants of 'Stairway to Heaven'.
2. Plants of the new *Polemonium* and 'Stairway to Heaven' differ in leaf color as plants of 'Stairway to Heaven' have white and grey variegated leaves.

BRIEF DESCRIPTION OF THE PHOTOGRAPHS

The accompanying photographs illustrate the overall appearance of the new *Polemonium* plant showing the colors as true as it is reasonably possible to obtain in colored reproductions of this type. Colors in the photographs may differ slightly from the color values cited in the detailed botanical description which accurately describe the colors of the new *Polemonium* plant.

The photograph on the first sheet is a top perspective view of typical flowering plants of 'Polelodge' grown in an outdoor nursery.

The photograph on the second sheet is a close-up view of a typical flowering plant of 'Polelodge'.

DETAILED BOTANICAL DESCRIPTION

The aforementioned photographs and following observations and measurements describe plants grown in 5-liter containers and ground beds in an outdoor nursery in Bressingham, Diss, Norfolk, United Kingdom and under cultural practices typically used in commercial *Polemonium* production. During the production of the plants, day temperatures ranged from 5° C. to 25° C. and night temperatures ranged from −6° C. to 15° C. Plants were 15 months old when the photographs and description were taken. In the following description, color references are made to The Royal Horticultural Society Colour Chart, 2000 Edition, except where general terms of ordinary dictionary significance are used.

Botanical classification: *Polemonium reptans* 'Polelodge'.

Parentage:

*Female, or seed, parent*.—Unnamed selection of *Polemonium reptans*, not patented.

*Male, or pollen, parent*.—Unknown selection of *Polemonium reptans*, not patented.

Propagation:

*Type*.—By basal cuttings.

*Time to initiate roots, summer*.—About ten days at soil temperatures about 15° C. and ambient temperatures about 18° C.

*Time to produce a rooted young plant, summer*.—About 20 days at soil temperatures about 15° C. and ambient temperatures about 18° C.

*Root description*.—Fine, fibrous; close to 158C in color.

*Rooting habit*.—Freely branching; dense.

Plant description:

*Plant and growth habit*.—Herbaceous perennial; basal clumping habit; dense and bushy appearance; moderately vigorous growth habit.

*Plant height*.—About 45 cm.

*Plant width* (*spread*).—About 60 cm to 70 cm.

Leaf description:

*Arrangement*.—Compound with about eight to 20 leaflets per leaf.

*Leaf length*.—About 15 cm to 25 cm.

*Leaf width*.—About 2.5 cm to 3.5 cm.

*Leaflet length*.—About 2 cm to 6 cm.

*Leaflet width*.—About 0.5 cm to 1.5 cm.

*Leaflet shape*.—Elliptical.

*Leaflet apex*.—Acute.

*Leaflet base*.—Cuneate.

*Leaflet margin*.—Entire.

*Leaflet texture and luster, upper and lower surfaces*.—Pubescent; dull.

*Leaflet venation pattern*.—Pinnate.

*Color*.—Developing leaves (spring), upper and lower surfaces: Variegated, close to 70A and 3B. Fully expanded leaves (summer and autumn), upper and lower surfaces: Variegated, close to 146C and 3C; occasionally during the summer, leaves will be solid yellow, close to 3B or 3C; venation, close to 145D.

*Petioles*.—Length: About 20 cm. Diameter: About 3 mm. Texture and luster, upper and lower surfaces: Smooth, glabrous; dull. Color, upper and lower surfaces: Close to 146C.

Flower description:

*Flower type and flowering habit*.—Single rotate flowers arranged in compound cymes; flowers face mostly outwardly; freely flowering habit with about 130 flowers developing per plant during the flowering season.

*Fragrance*.—Faintly fragrant.

*Natural flowering season*.—Long flowering period, plants flower continuously from May to July in the United Kingdom.

*Flower longevity*.—Flowers last about 20 days on the plant; flowers not persistent.

*Flower buds*.—Height: About 5 mm. Diameter: About 3 mm. Shape: Obovate. Texture and luster: Smooth; dull. Color: Close to 3B or 3C.

*Inflorescence height*.—About 25 cm.

*Inflorescence diameter*.—About 4 cm.

*Flower diameter*.—About 1 cm.

*Flower depth*.—About 1.5 cm.

*Petals*.—Quantity per flower: Typically five in a single whorl. Length: About 5 mm. Width: About 5 mm. Shape: Orbicular. Apex: Rounded. Base: Cuneate. Margin: Entire. Texture and luster, upper and lower surfaces: Smooth, glabrous; satiny; dull. Color: When opening, upper and lower surfaces: Close to 92C. Fully opened, upper and lower surfaces: Close to 92D; venation, close to 92B; color does not change with development.

*Sepals*.—Quantity per flower: Typically five in a single whorl, fused towards the base; calyx, campanulate. Length: About 6 mm. Width: About 3 mm. Shape: Lanceolate. Apex: Acute. Margin: Entire. Texture and luster, upper and lower surfaces: Smooth, glabrous; dull. Color: When opening, upper and lower surfaces: Close to 3B or 3C. Fully opened, upper and lower surfaces: Close to 3B to 3C.

*Pedicels*.—Length: About 5 mm. Diameter: About 3 mm. Strength: Moderately strong. Texture and luster: Smooth, glabrous; dull. Color: Close to 146C.

*Reproductive organs*.—Stamens: Quantity per flower: Typically five. Filament length: About 5 mm. Filament color: Close to 16A. Anther size: About 3 mm by 1 mm. Anther shape: Tubular. Anther color: Close to 16A. Pollen amount: Scarce. Pollen color: Light yellowish orange. Pistils: Quantity per flower: One. Pistil length: About 5 mm. Stigma shape: Tubular. Stigma color: Close to 150D. Style length: About 3 mm. Style color: Close to 150D. Ovary color: Close to 150D.

*Seeds*.—Quantity per flower: About three. Length: About 3 mm. Diameter: About 1 mm. Texture: Slightly rough. Color: Close to 166D.

Garden performance: Plants of the new *Polemonium* have been observed to have good garden performance and tolerate rain, wind, temperatures ranging from about −15° C. to about 30° C. and to be suitable for USDA Hardiness Zones 3 through 9.

Pathogen & pest resistance: Plants of the new *Polemonium* have been not been observed to be resistant to pathogens and pests common to *Polemonium* plants.

It is claimed:

1. A new and distinct *Polemonium* plant named 'Polelodge' as illustrated and described.

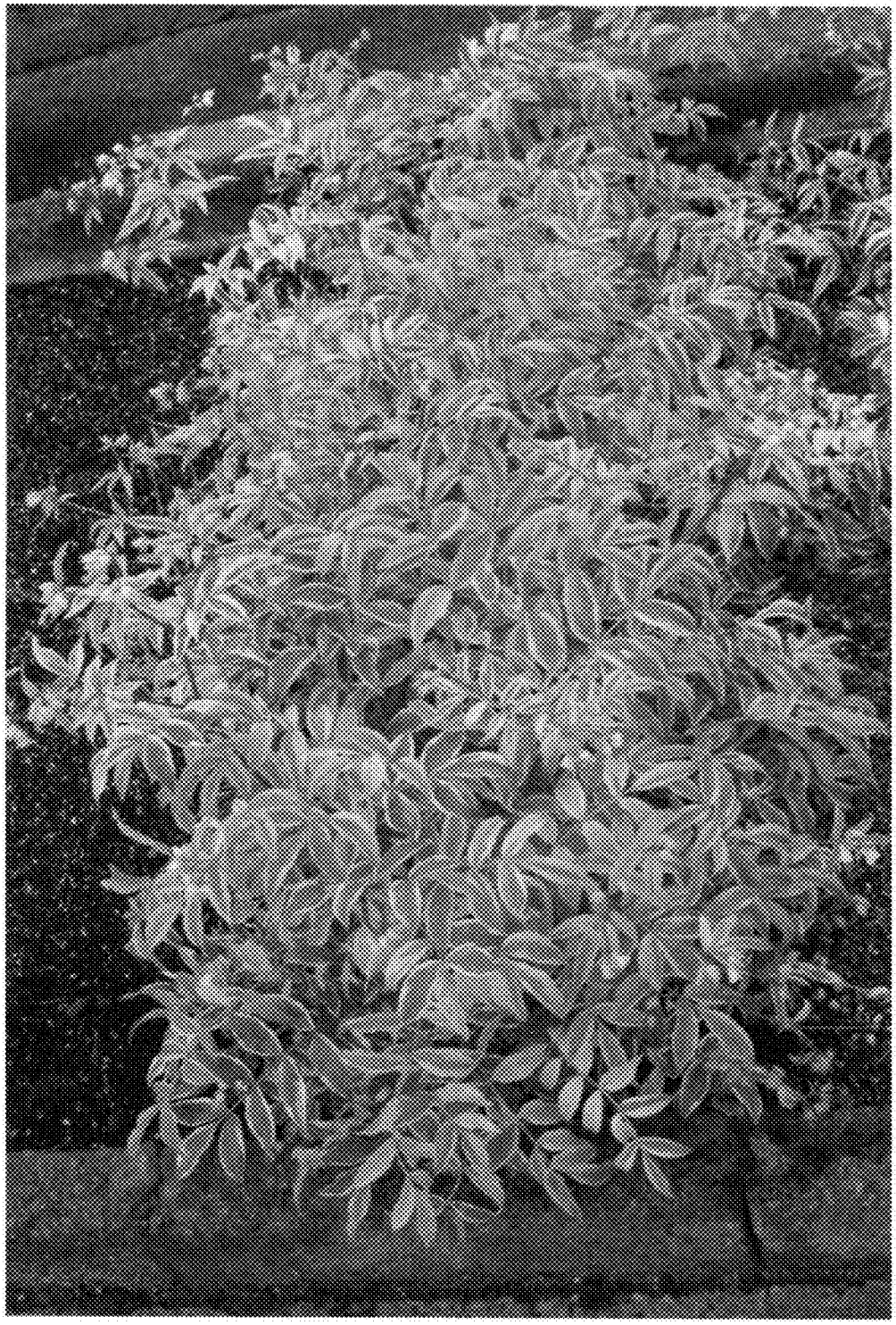

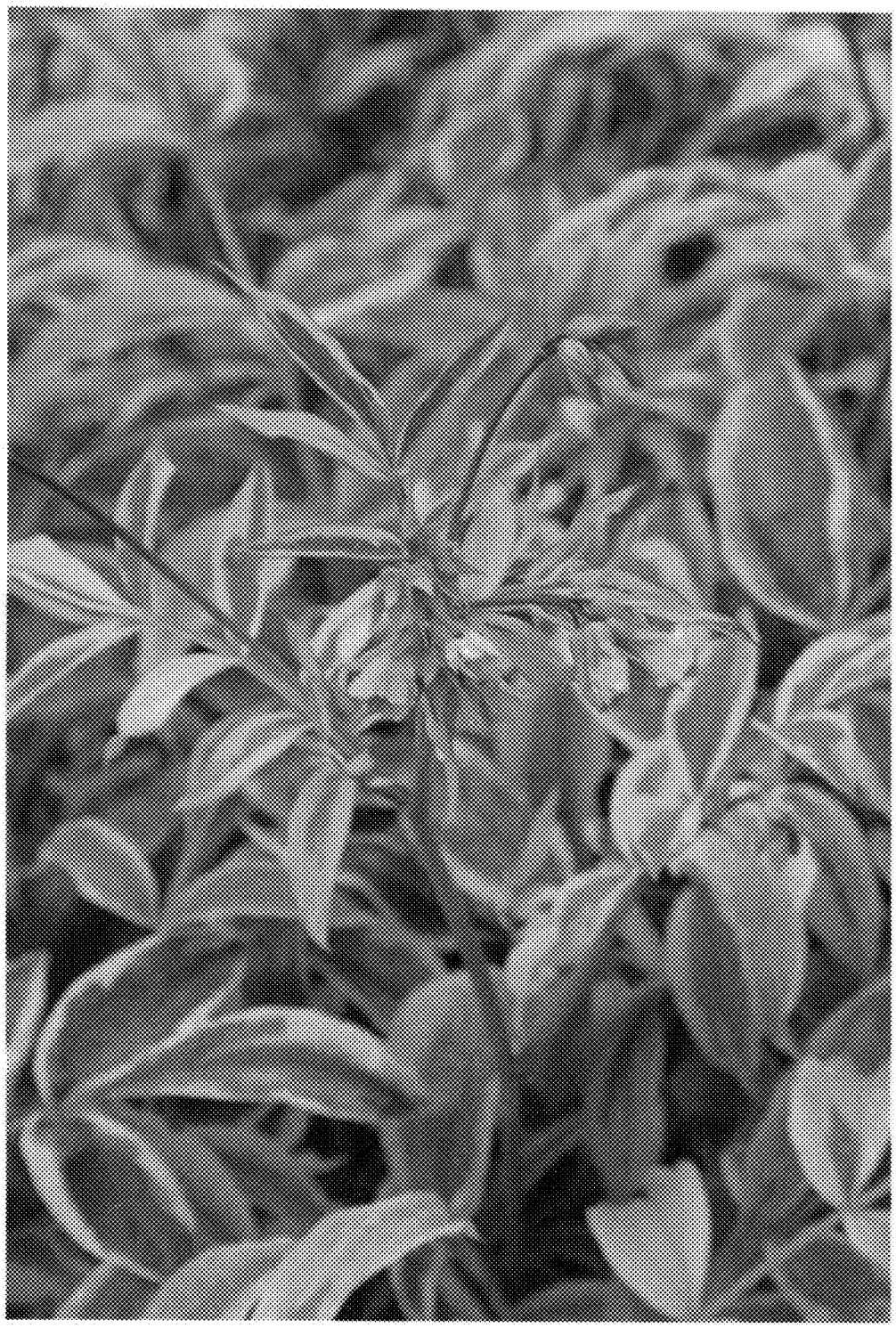

* * * * *